(12) United States Patent
Medema

(10) Patent No.: US 6,400,984 B1
(45) Date of Patent: Jun. 4, 2002

(54) METHOD AND APPARATUS FOR DETECTING WHETHER A LOAD IS A PATIENT OR A TEST DEVICE

(75) Inventor: Douglas K. Medema, Everett, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 117 days.

(21) Appl. No.: 09/590,459

(22) Filed: Jun. 9, 2000

(51) Int. Cl.[7] ............................................. A61N 1/39
(52) U.S. Cl. .............................................. 607/8; 607/7
(58) Field of Search .......................................... 607/7, 8

(56) References Cited

U.S. PATENT DOCUMENTS

| | | | |
|---|---|---|---|
| 3,747,605 A | 7/1973 | Cook | 607/8 |
| 3,789,834 A | 2/1974 | Duroux | 600/407 |
| 4,780,661 A | 10/1988 | Bolomey et al. | 324/638 |
| 4,840,177 A | 6/1989 | Charbonnier et al. | 607/8 |
| 5,088,489 A | 2/1992 | Lerman | 607/7 |
| 5,203,344 A | 4/1993 | Scheltinga et al. | 600/547 |
| 5,503,157 A | 4/1996 | Sramek | 600/506 |
| 5,632,267 A | 5/1997 | Högnelid et al. | 607/5 |
| 5,662,687 A | 9/1997 | Hedberg et al. | 607/5 |
| 5,836,978 A | 11/1998 | Gliner et al. | 607/7 |
| 5,999,852 A * | 12/1999 | Elabbady et al. | 607/8 |
| 6,058,325 A * | 5/2000 | Baura | 607/8 |
| 6,198,967 B1 * | 3/2001 | Brewer et al. | 607/7 |

* cited by examiner

Primary Examiner—Carl Layno
(74) Attorney, Agent, or Firm—Christensen O'Connor Johnson Kindness PLLC

(57) ABSTRACT

A method and apparatus that automatically detects whether a load connected to a defibrillator is a patient or a test device measures a load-dependent electrical parameter, such as impedance, by delivering to the load at least two small-amplitude signals, each having different frequencies. Because the impedance of a patient is complex, impedance measurements obtained from the small-amplitude signals delivered to the load will differ if the load is a patient. If the impedance measurements obtained from the small-amplitude signals are approximately equal, the load is determined to be a test device. In an alternative embodiment, a small signal impedance measurement may be compared with an impedance measurement obtained from application of a high-amplitude signal to the load. Differing measurements indicate that the load is a patient, while impedance measurements that are approximately equal indicate that the load is a test device. If the load is a test device, a defibrillator implementing the present device may selectively determine to not store data in a memory, which data is normally collected and stored by the defibrillator while connected to a patient. A voting scheme may also be used to compare the measured load-dependent electrical parameters and determine the nature of the load when three or more signals are delivered to the load.

23 Claims, 4 Drawing Sheets

METHOD AND APPARATUS FOR DETECTING WHETHER A LOAD IS A PATIENT OR A TEST DEVICE

FIELD OF THE INVENTION

The invention relates generally to medical devices and, more particularly, to a method and apparatus for detecting whether a load connected to an external defibrillator is a patient or a test device.

BACKGROUND OF THE INVENTION

Ventricular fibrillation is one of the most common life-threatening medical conditions that occurs with respect to the human heart. A common treatment for ventricular fibrillation is to apply an electric pulse to the heart that is strong enough to stop the heart's unsynchronized electrical activity and give the heart a chance to reinitiate a synchronized rhythm. External defibrillation refers to a method of applying an electric pulse to a fibrillating heart through the surface of a patient's body.

When a defibrillation pulse is applied to a patient, the pulse encounters a resistance to the flow of electrical current through the patient. The resistance of a patient's thorax to the flow of electrical current is called transthoracic impedance (TTI). The magnitude of current flowing through a patient is directly proportional to the magnitude of the voltage difference across the electrodes used to deliver the defibrillation pulse to the patient and inversely proportional to the patient's TTI.

A patient's TTI is comprised of two components: resistance and reactance. The conductive characteristic of body fluids provides the resistive component, whereas cell membranes, acting as imperfect capacitors, contribute to the reactive component. An impedance that includes both resistance and reactance is known as a complex impedance.

The measurement of a patient's TTI varies according to the amplitude of the electric signal applied to the patient. The impedance encountered by a small-amplitude signal applied to a patient is different than the impedance encountered by a high-amplitude signal (e.g., a defibrillation pulse).

Advances in defibrillation technology have found that defibrillation therapy may be optimized by adjusting the magnitude and duration of a defibrillation pulse according to the patients defibrillation impedance (i.e., the impedance encountered by a defibrillation pulse applied to the patient). While an initial defibrillating pulse may be applied to a patient in order to measure the patient's defibrillation impedance, it is preferable that the initial defibrillation pulse already be optimized according to the patient's defibrillation impedance. A suitable method for predicting a patient's defibrillation impedance involves first sending a small-amplitude signal through the electrodes of the defibrillator and measuring the impedance encountered by the small-amplitude signal. A transformation equation is then applied to the small signal impedance measurement to produce a predicted defibrillation impedance of the patient. A transformation equation of this type is typically generated by correlating small signal impedance measurements previously obtained for a population of patients with high-amplitude (i.e., defibrillation) impedance measurements obtained for the same population.

While applying a transformation equation to a small signal impedance measurement is useful in predicting a patient's defibrillation impedance, a problem arises when testing the defibrillator on a test device, or test load, instead of a patient. A typical test device for testing a defibrillator is comprised of a high-power 50 ohm resistor intended to represent the patient. A defibrillation pulse is discharged from the defibrillator into the test device and measured to ensure that the defibrillator is working properly. Because the resistor in a test device has only a resistive component, and does not present a complex impedance to the defibrillator, the measured impedance of the test device does not vary with the amplitude of the electric signal applied to the device. In other words, a test device's "defibrillation impedance" will be the same as the measured small signal impedance.

Unless a defibrillator is manually set in a "test" mode of operation, the defibrillator does not know that a test device (as opposed to a patient) is connected to the defibrillator. Consequently, when the defibrillator applies a transformation equation to a small signal impedance measurement of a test device to "predict" the test device's defibrillation impedance, an incorrect predicted impedance is produced. This incorrect defibrillation impedance is then used to shape the defibrillation waveform that is delivered to the test device, resulting in the wrong amount of energy being delivered to the test device.

Furthermore, a defibrillator typically collects data relating to the delivery of a defibrillation pulse and stores this data in a memory for later review by medical professionals and others. However, a defibrillator's memory is limited in size and often holds only the most recent data collected by the defibrillator. In a test situation where a test device is attached to the defibrillator, it may be undesirable to store the generated data and overwrite earlier data relating to defibrillation pulses delivered to actual patients.

Accordingly, there is a need for a method and apparatus that can automatically differentiate when a test device, as opposed to a patient, is connected to a defibrillator. The present invention addresses the this need and other shortcomings in the prior art.

SUMMARY OF THE INVENTION

A device constructed in accordance with the present invention automatically detects whether a load that is connected (or to be connected) to a defibrillator is a patient or a test device. The device assists in deciding when a transformation equation should be used to predict the defibrillation impedance of the load. The transformation equation is applied to a small signal impedance measurement of the load when the device determines that the load is a patient.

The device of the present invention also assists in deciding when data collected by a defibrillator while connected to a test load should be saved in a memory. If the load connected to a defibrillator is determined to be a test device, the defibrillator may selectively not save data generated while connected to the test device, thus preserving memory space in the defibrillator for data relating to defibrillation therapy delivered to actual patients.

A device constructed according to the present invention may be implemented as a stand-alone device or as an integral part of a defibrillator or other medical device. In one embodiment of the invention, a defibrillator (or other device embodying the invention) utilizes at least two small-amplitude signals having different frequencies to measure at least two load-dependent electrical parameters of the load. Suitable load-dependent electrical parameters include small signal impedance measurements of the load. The small signal impedance measurements are compared to each other to determine the nature of the load.

Because a patient presents a complex impedance to an electric signal (in contrast to a test device that presents only a purely resistive impedance), small signal impedance measurements of a load that is a patient will differ according to the frequencies of the small-amplitude signals used to measure the patient's impedance. Thus, a load is determined to be a patient if the small signal impedance measurements of the load are not approximately equal.

On the other hand, a test device presents only a resistive impedance to the defibrillator. When measuring the impedance of a test device using small-amplitude signals of different frequencies, there will be little or no appreciable difference in the small signal impedance measurements of the load. Consequently, if the small signal impedance measurements of a load are approximately equal, the defibrillator determines that the load is a test device.

In an alternative embodiment of the invention, a small signal impedance measurement obtained prior to defibrillation may be compared with a high-amplitude signal impedance measurement (e.g., defibrillation magnitude pulse), to determine the nature of the load. If the load is a patient, the impedance measurements will differ. If the load is a test device, the impedance measurements will be approximately equal.

In accordance with one aspect of the invention, if the defibrillator determines that the load is a patient, the defibrillator may automatically apply a transformation equation to one or both (or some combination) of the small signal impedance measurements to predict the high-amplitude defibrillation impedance of the load (i.e., patient). Using a predicted defibrillation impedance of the patient, the defibrillator may adjust the amplitude and duration of the defibrillation pulse to be applied to the patient to compensate for the patient's particular impedance, and thus increase the effectiveness of the defibrillation pulse to be applied to the patient.

In accordance with another aspect of the invention, if the defibrillator determines that the load is a test device, the defibrillator may proceed to prepare and deliver a defibrillation pulse with amplitude and duration characteristics optimized for the measured small signal impedance of the load without applying a transformation equation as discussed above. The defibrillator may also automatically enter into a test mode or calibration mode of operation. In this mode of operation, the defibrillator may provide an option of not saving data normally collected and stored by the defibrillator while connected to a patient. Alternatively, the defibrillator may be configured to automatically not save such data if the load is determined to be a test device.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

A defibrillator implementing the present invention automatically determines whether a load connected to the defibrillator is a patient or a test device, prior to delivering a defibrillation pulse to the load. Although the exemplary embodiment of the invention described herein is implemented in a defibrillator, such implementation is not required. The invention may be implemented as a stand-alone device or in another type of medical device. If implemented in a separate device, the device preferably includes a communication link with the defibrillator to communicate whether the load is a patient or a test device, and other information such as measurements of the patient's impedance. The communication link may use conventional wire-based or wireless communication technology.

Briefly stated, a defibrillator constructed according to one embodiment of the present invention measures a load-dependent electrical parameter of the load, such as impedance, by sending at least two small-amplitude signals having different frequencies through electrodes placed on the load. If the load is a patient, the patient's complex impedance, when measured, will vary with the frequency of the impedance measuring signal. If the load is a test device, there will be little or no appreciable difference in measured impedance, regardless of the signal frequencies used. While inductance in the cables used to connect the load to the defibrillator may cause small differences to appear in the measured impedance, the differences are much smaller for a test device than the difference in impedance that results from a patient being connected to the defibrillator.

If the defibrillator determines that the load is a patient, the defibrillator may apply a transformation equation to the impedance measurements obtained from the small-amplitude signals to predict the patient's high-amplitude (i.e., defibrillation-magnitude) impedance. Predicting the patient's defibrillation impedance allows the defibrillator to optimize a defibrillation pulse according to the patient's defibrillation impedance prior to delivery of the pulse to the patient. If the load is a test device, the defibrillator may deliver a defibrillation pulse to the load based on the small signal impedance measurement of the load, without applying a transformation equation to the impedance measurement.

Figure 1:
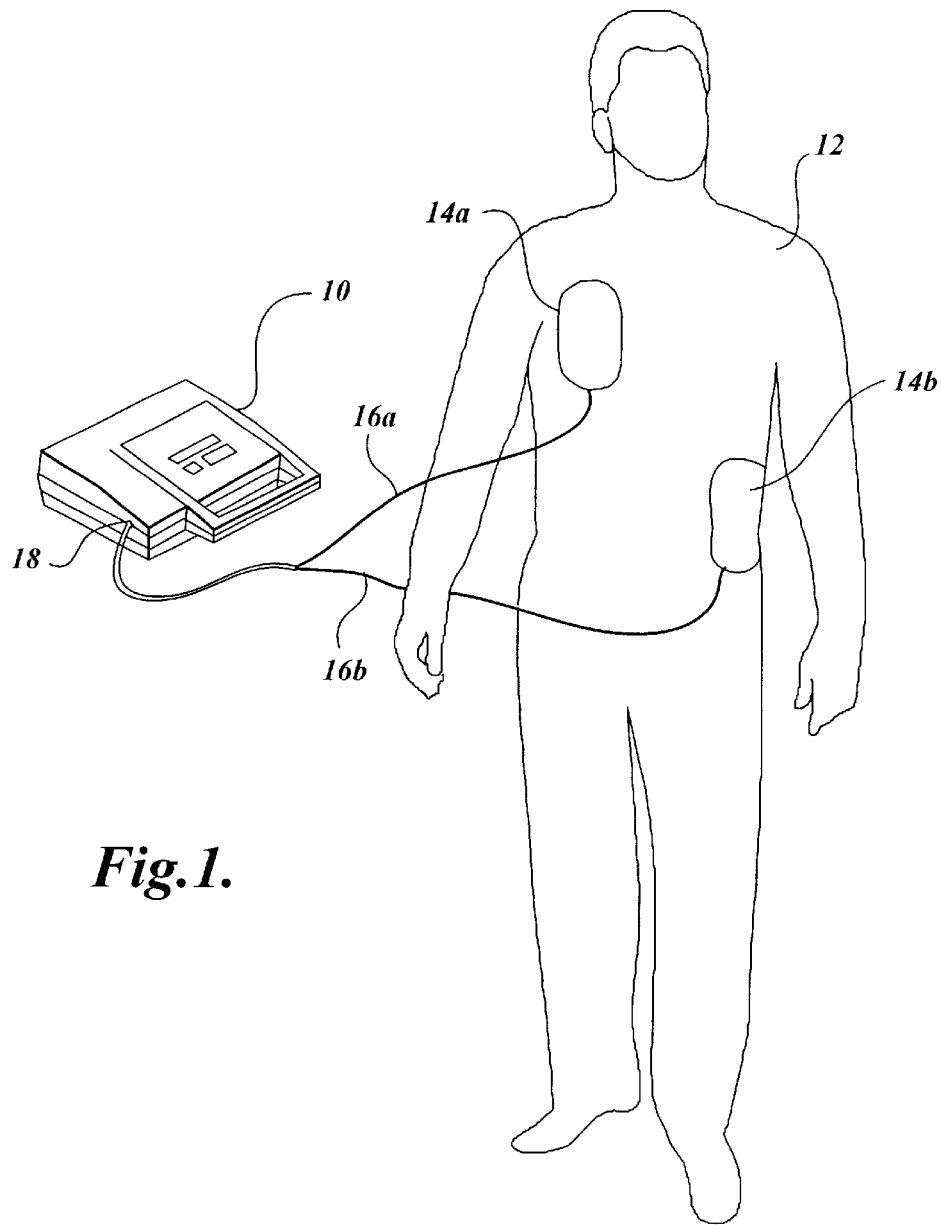
FIG. 1 is a pictorial diagram of a defibrillator constructed in accordance with the present invention and connected to a patient for defibrillation.

FIG. 1 illustrates an external defibrillator 10 constructed in accordance with the present invention. The defibrillator 10 is connected to a patient 12 by way of electrodes 14a and 14b placed on the body of the patient 12. The electrodes 14a and 14b are connected to a terminal 18 on the defibrillator 10 via cables 16a and 16b. The electrodes 14a and 14b are placed on the patient 12 in accordance with accepted practice for delivering a defibrillation pulse.

Figure 2:
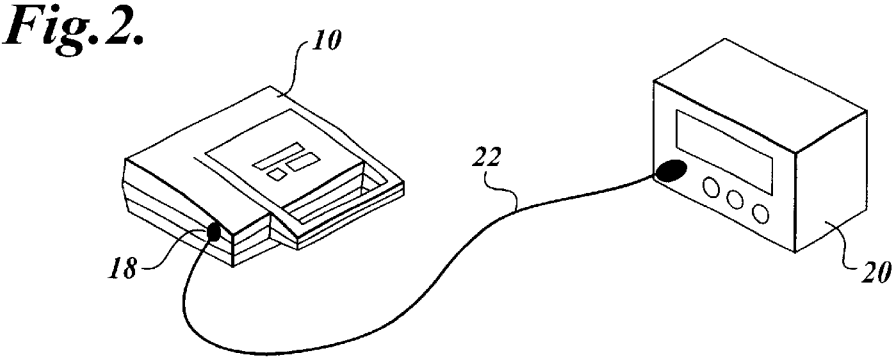
FIG. 2 is a pictorial diagram of the defibrillator shown in FIG. 1 connected to a test device.

FIG. 2, on the other hand, illustrates the connection of a test device 20 to the defibrillator 10. The test device 20 shown in FIG. 2 is connected directly to the terminal 18 of the defibrillator 10 via cable 22. The test device 20 is designed to evaluate whether the defibrillator 10 is operating correctly (e.g., by measuring a defibrillation pulse delivered by the defibrillator 10 to the test device 20).

Figure 3:
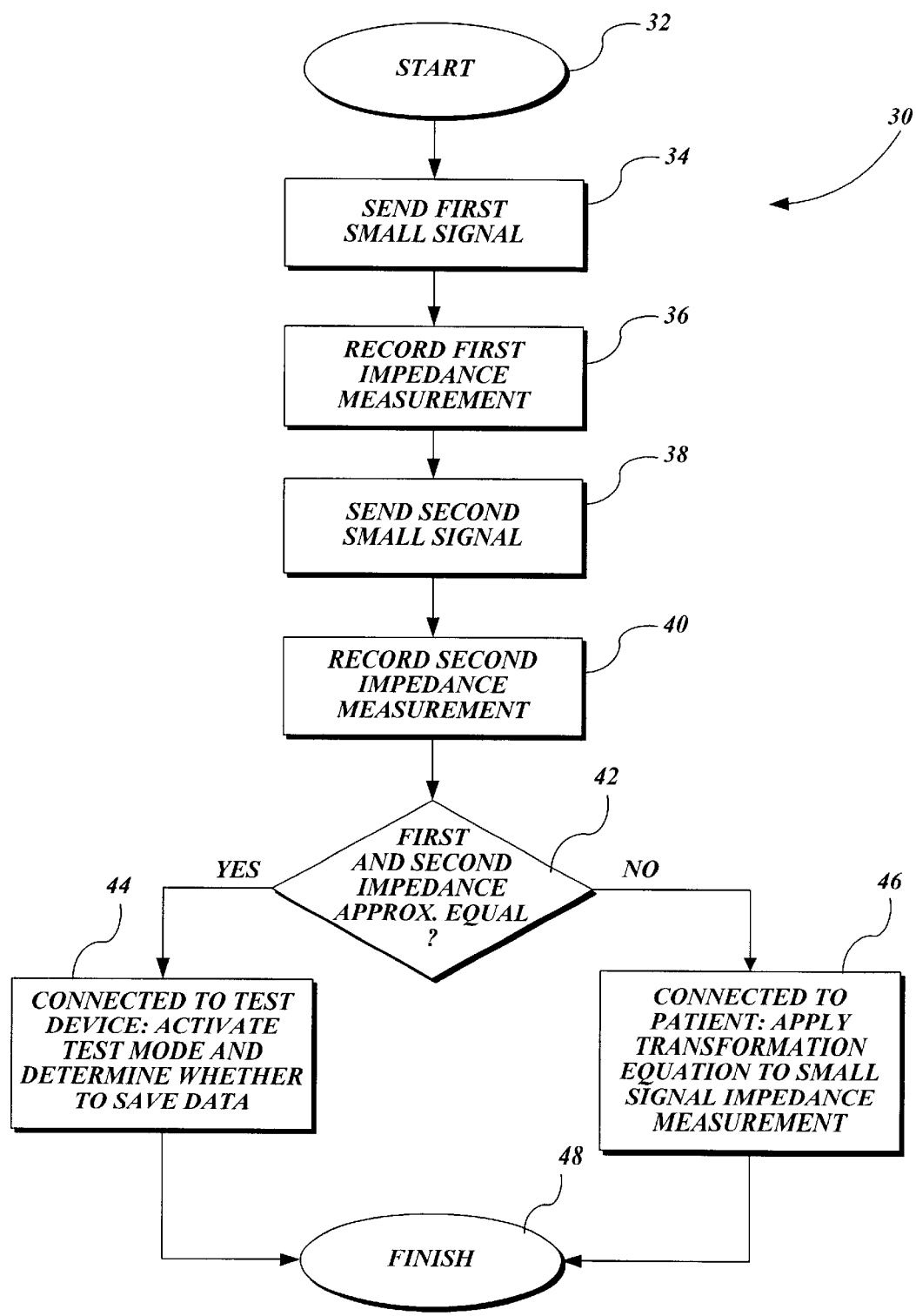
FIG. 3 is a flow chart illustrating a method according to the present invention for determining whether a patient or a test device is connected to a defibrillator as shown in FIGS. 1 and 2.

Initially, the defibrillator 10 does not know whether a load connected to the defibrillator is a patient 12 or a test device 20. FIG. 3 depicts a process 30 according to the present invention for determining whether a patient 12 or a test device 20 is connected to the defibrillator 10.

The process 30 begins at a block 32 in which a load (i.e., a patient 12 or test device 20) has already been connected to the defibrillator 10. At a block 34, prior to delivering a defibrillation pulse to the load, the defibrillator 10 delivers the first of at least two small-amplitude signals at a first frequency to the load (e.g., via cables 16a and 16b and electrodes 14a and 14b, or via cable 22, as shown respectively in FIGS. 1 and 2). Testing has revealed that electric signals whose amplitudes are small enough, e.g., 100–150 microamps, are generally not felt or noticed by patients. By using small-amplitude signals of this order to measure the impedance of the load, it is unnecessary to deliver defibrillation magnitude pulses to the load for the purpose of impedance measurement. A small signal measure of the impedance of the load may be obtained by measuring the voltage drop across the load when the small-amplitude signal is applied to the load. After the first small signal impedance measurement of the load is obtained, the process 30 proceeds to a block 36, where the impedance measurement is recorded. The small signal impedance measurement may be recorded in an internal memory 76 (FIG. 5), such as a random-access memory or a disk memory implemented in the defibrillator 10, or may be recorded in a memory located in another device that communicates with the defibrillator 10.

Proceeding to block 38, the defibrillator 10 sends a second small-amplitude signal at a second frequency to the load. The frequency of the second small-amplitude signal is sufficiently different than the frequency of the first small-amplitude signal so that if a patient, having a complex impedance, is attached to the defibrillator 10, the defibrillator 10 will detect a difference in measured impedance. Frequencies of approximately 14 kHz and 62 kHz are contemplated for one actual embodiment of the invention that utilizes two impedance measuring signals. Other embodiments of the invention may use a different number of small-amplitude signals at different frequencies without departing from the scope of the present invention. Once the second small-amplitude signal is delivered to the load and the second small signal impedance measurement is obtained, the process 30 proceeds to a block 40.

At block 40, the second small signal impedance measurement is recorded in a manner similar to that of the first small signal measurement, as described in block 36. The measuring and recording actions taken in blocks 34 and 36 (and/or blocks 38 and 40) may be repeated any number of times to produce any number of small signal impedance measurements of the load. Once at least a second small signal impedance measurement is recorded in block 40, the process 30 may proceed to a decision block 42.

At decision block 42, the defibrillator 10 compares the small signal impedance measurements to one another. As noted earlier, impedance measurements obtained at the different signal frequencies will be different the load is a patient 12. If the load is a test device 20, the impedance measurements will be approximately equal, regardless of the signal frequencies used. For example, in testing, impedance measurements of patients have been found to differ by about 5% when using small-amplitude impedance measuring signals at frequencies of 15 kHz and 20 kHz. When measuring load impedance using signals at these frequencies, a difference of impedance that is less than 5% may be interpreted as "approximately equal," and therefore result in a determination that the load is a test device. Conversely, a difference of impedance equaling or exceeding 5% at these frequencies may result in a determination that the load is a patient. For signal frequencies of 15 kHz and 20 kHz, a 5% difference in measured impedance may thus be used as a threshold to differentiate between a patient and a test device. A patient's impedance measurement generally decreases as the frequency of the impedance measuring signal applied to the patient increases.

If, at decision block 42, the small signal impedance measurements are found to be approximately equal, the process 30 proceeds to a block 44. At block 44, the defibrillator 10 determines that the load is a test device 20. The defibrillator 10 then proceeds to the next proper task for delivery of a defibrillation pulse to the test device 20. For example, the defibrillator 10 may immediately deliver a defibrillation pulse to the test device 20 without applying a transformation equation normally used to convert a small signal impedance measurement of the load to a predicted defibrillation impedance.

The defibrillator 10 may also provide a choice to the operator of the defibrillator to not save data normally collected and stored by the defibrillator while connected to a patient. By not saving data collected in a test situation, the operator may preserve memory space in the defibrillator 10. In this manner, the operator may preserve data previously recorded in the defibrillator 10 that otherwise might have been overwritten to store the data collected in the current test situation. The defibrillator 10 may also be set to automatically not save data when the load is determined to be a test device.

In addition, the defibrillator 10 may indicate via an output, such as a display screen, that the defibrillator has entered a test mode of operation (e.g., by displaying the phrase "Test Mode" or lighting a selected LED). Those of ordinary skill in the art will appreciate that any number of actions may be taken following a determination that the defibrillator 10 is connected to a test device 20. These actions are not limited to the specific examples given. Once the defibrillator 10 has determined that it is connected to a test device 20 and has performed actions corresponding to that determination, the process 30 proceeds to a block 48 where the process 30 is finished.

Returning to decision block 42, if the small signal impedance measurements are not found to be approximately equal (e.g., the difference in impedance equals or exceeds about 5% when measured using signals at 15 kHz and 20 kHz), the process 30 proceeds to a block 46. At block 46, the defibrillator 10 determines that the load is a patient 12. Based on that determination, the defibrillator 10 may automatically apply a transformation equation to one or both of the impedance measurements, or a combination (e.g., an average or a median) of the impedance measurements, to predict the patient's defibrillation impedance.

In another aspect of the present invention, the defibrillator 10 may adjust the amplitude and duration of the defibrillation pulse to be delivered to the patient based on the patient's predicted defibrillation impedance. The defibrillator 10 thus tailors the defibrillation pulse for the particular patient. In one embodiment of the invention, the defibrillator 10 includes a memory (e.g., memory 76 shown in FIG. 5) that contains a table of values representing voltage levels to which a capacitor bank in the defibrillator 10 should be charged for different values of predicted defibrillation impedance. The memory also contains a table of values representing phase duration for different values of predicted defibrillation impedance. The table of voltage levels and table of phase durations may advantageously be combined into a single table. The defibrillator 10 uses a patient's predicted defibrillation impedance as an index to the table to identify an appropriate voltage level to which its capacitor bank should be charged and an appropriate phase duration for delivering a defibrillation pulse to the patient. While, if desired, an interpolation algorithm can be used to determine a precise voltage level and phase duration for each possible predicted defibrillation impedance, ranges of predicted defibrillation impedance may also be used to select appropriate voltage and phase duration values. For example, if a predicted defibrillation impedance lies in a specific range, e.g., 45–50 ohms, a particular voltage level and phase duration value that corresponds with that range is read from the table. If the predicted defibrillation impedance falls in another range, e.g., 70–75 ohms, a different voltage level and phase duration value may be read from the table. When using ranges, corrections for quantization errors may be appropriate. A suitable method for adjusting defibrillation waveform characteristics, such as amplitude and duration, in response to patient impedance is described in more detail in U.S. Pat. No. 5,999,852, titled "Defibrillator Method and Apparatus," which has been assigned to the assignee of the present invention and is incorporated herein by reference.

Any number of actions may be taken following a determination that the load is a patient 12. These actions are not limited to the specific examples given above. Once the defibrillator 10 determines that it is connected to a patient 12 and performs actions corresponding to that determination (such as applying a transformation equation to a small signal impedance measurement), the process 30 proceeds to block 48 where the process 30 is finished. At that point, the defibrillator 10 may return to a state where it is ready to deliver another defibrillation pulse to the patient 12, with or without remeasuring the patient's impedance.

As noted above, a device, such as a defibrillator, constructed according to the present invention may apply any number of small-amplitude signals at different frequencies to measure the impedance of the load. If three or more impedance-measuring signals are used, the device may implement a voting scheme to compare the impedance measurements to one another to determine whether the load is a patient or a test device. For example, as shown in FIG. 4, the defibrillator 10 may determine that the load is a test device if a majority of N impedance measurements are approximately equal (e.g., two out of three where N=3).

Figure 4:
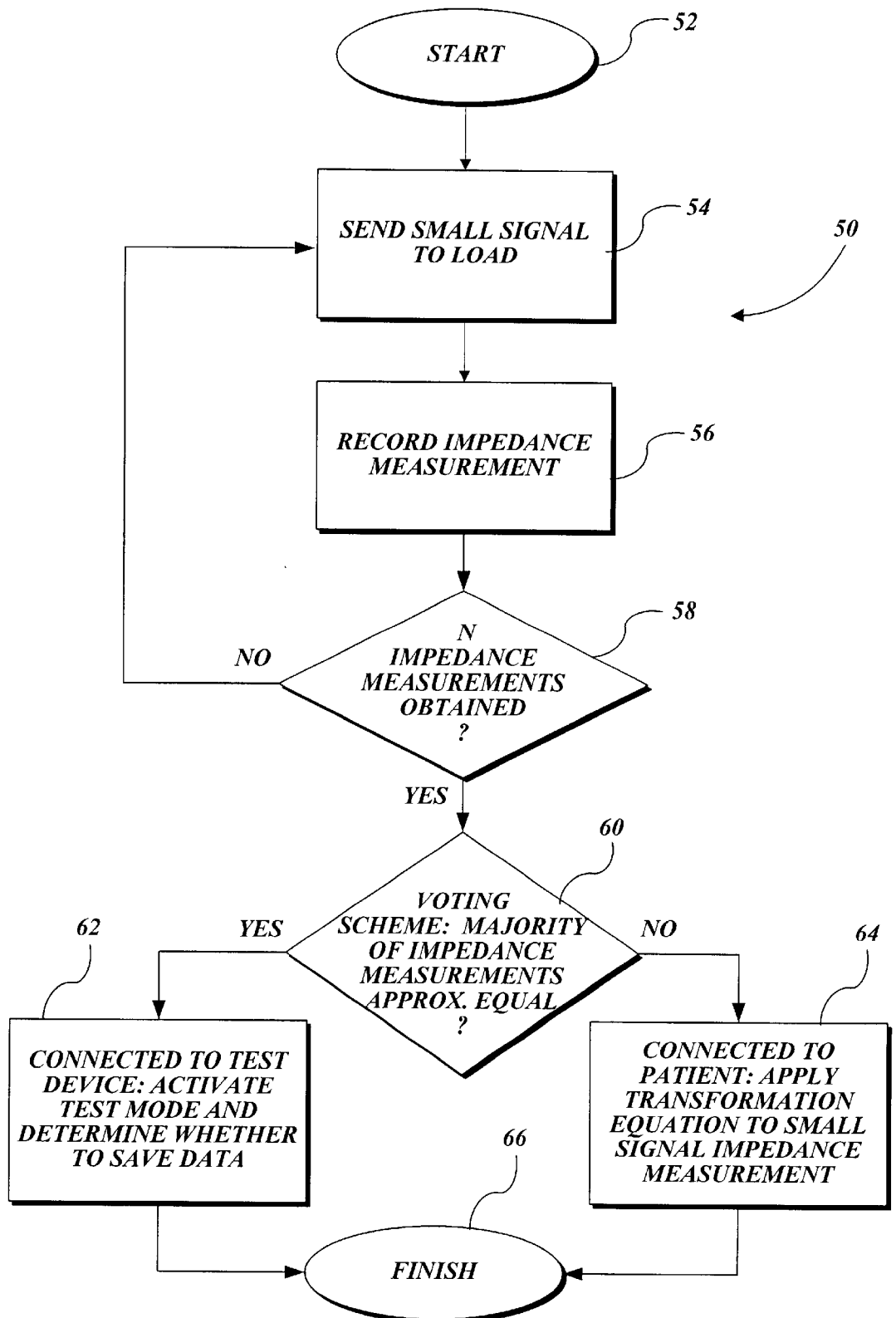
FIG. 4 is a flow chart illustrating a method according to the present invention in which a voting scheme is used in determining whether a load is a patient or a test device.

The process 50 illustrated in FIG. 4 begins at a block 52 where the load has been connected to the defibrillator 10. At a block 54, the defibrillator 10 sends a small-amplitude signal at a frequency to the load for the purpose of measuring a load-dependent electrical parameter of the load, such as a small signal impedance. At a block 56, the small signal impedance (or other load-dependent electrical parameter) is recorded in a memory. The procedure for sending a small-amplitude signal to the load (block 54) and recording an impedance measurement of the load (block 56) may be performed in a manner similar to that described with respect to blocks 34 and 36 in FIG. 3.

In a decision block 58, the defibrillator 10 determines whether a predetermined number N of impedance measurements have been obtained. If not, the defibrillator 10 returns to block 54 and sends another small-amplitude signal at a different frequency to the load. The small signal impedance measurement obtained using the different frequency signal is recorded in block 56. Decision block 58 once again evaluates whether N impedance measurements have been obtained. The process of sending small-amplitude signals at different frequencies to the load (block 54) and recording the resulting impedance measurements (block 56) is repeated until N impedance measurements are obtained.

The defibrillator 10 then proceeds from decision block 58 to a decision block 60 wherein the defibrillator 10 implements a voting scheme to evaluate the impedance measurements. For example, the defibrillator 10 may determine whether a majority of the N impedance measurements are approximately equal. If a majority of the N impedance measurements are approximately equal, the defibrillator 10 proceeds to a block 62, where the defibrillator 10 determines that the load is a test device 20. Once the defibrillator 10 has determined that it is connected to a test device 20 and has performed actions corresponding to that determination (e.g., as described with respect to block 44 in FIG. 3), the process 50 proceeds to a block 66 where the process 50 is finished.

Returning to decision block 60, if a majority of the N small signal impedance measurements are not found to be approximately equal, the process 50 proceeds to a block 64 where the defibrillator 10 determines that the load is a patient 12. Once the defibrillator 10 determines that it is connected to a patient 12 and performs actions corresponding to that determination (e.g., as described earlier with respect to block 46 in FIG. 3), the process 50 proceeds to block 66 where the process 50 is finished.

It will be appreciated that alternative voting schemes may be used in decision block 60 to evaluate the N small signal impedance measurements. For instance, the defibrillator 10 may require that a certain number of consecutive impedance measurements be approximately equal to determine that the load is a test device 20. The defibrillator 10 may also weight the differences of impedance measurements depending on the frequencies of the impedance measuring signals before determining whether the load is a patient 12 or a test device 20.

Figure 5:
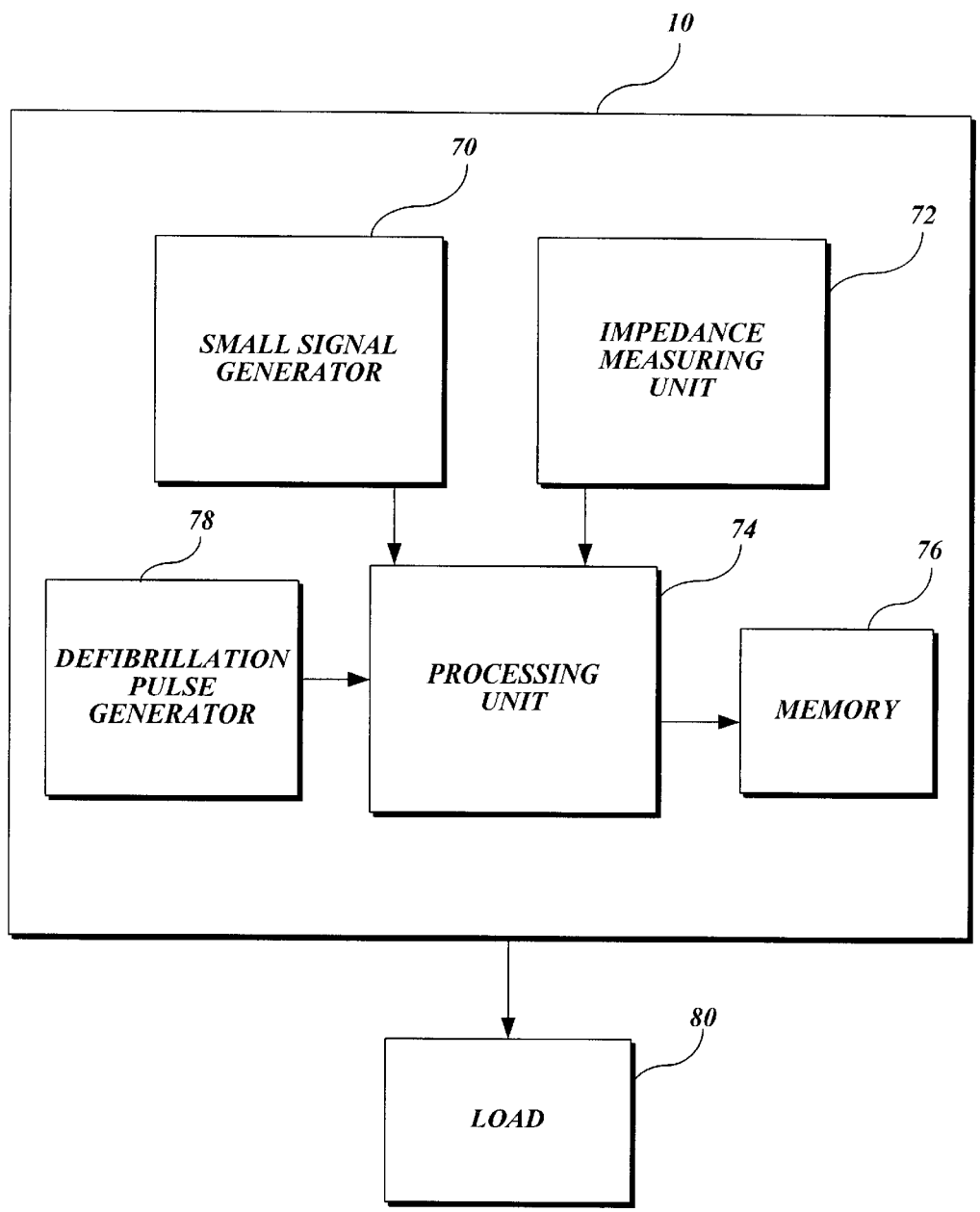
FIG. 5 is a block diagram depicting the major components of a defibrillator as shown in FIGS. 1 and 2, which is capable of implementing the methods illustrated in FIGS. 3 and 4.

FIG. 5 illustrates the major components of a defibrillator 10 capable of determining whether a load 80 connected to the defibrillator 10 is a patient 12 or a test device 20, in accordance with the present invention. The defibrillator 10 includes a small signal generator 70 adapted to deliver two or more small-amplitude signals at different frequencies to the load 80. A suitable small signal generator 70 may be selected from the many types of signal generators that are commercially available (i.e. off the shelf).

An impedance measuring unit 72 measures the impedance of the load 80 based on the small-amplitude signals delivered by the small signal generator 70 to the load 80. The impedance measuring unit 72 monitors a load-dependent electrical parameter resulting from delivery of the small signals to the load, such as voltage drop, current flow, energy delivered, load-defibrillator time constant, etc. If desired, the load-dependent electrical parameter may then be used to determine the small signal impedance of the load. In terms of implementation, the impedance measuring unit 72 may be comprised of discrete electronic components, or may be comprised of a processing unit operating according to programmed instructions. If implemented as the latter, the processor forming the impedance measuring unit 72 may be advantageously combined with the processing unit 74 discussed below.

The processing unit 74 illustrated in FIG. 5 instructs the small signal generator 70 to deliver the small-amplitude signals to the load 80 and receives the resulting small signal impedance measurements from the impedance measuring unit 72. The processing unit 74 compares the small signal impedance measurements to each other to determine whether they are approximately equal. If the impedance measurements are different, the processing unit 74 determines that the load 80 is a patient. If the impedance measurements are approximately equal, the processing unit 74 determines that the load 80 is a test device. If the load 80 is determined to be a patient, the processing unit 74 may apply a transformation equation to one or more (or a combination) of the small signal impedance measurements to predict the high-amplitude defibrillation impedance of the load 80.

The defibrillator 10 also includes a memory 76 and a defibrillation pulse generator 78. The memory 76 is used to store impedance measurements received from the impedance measuring unit 72 and other data collected by the defibrillator 10. The memory 76 may also be used to store programmed instructions that direct the operation of the processing unit 74 in accordance with the present invention. Any combination of volatile storage (e.g., RAM) and non-volatile storage (e.g., flash memory or hard disk) may be used to implement the memory 76.

The defibrillation pulse generator 78 is configured to deliver a defibrillation pulse to the load 80. Preferably, the defibrillation pulse generator is configured to tailor characteristics of the defibrillation pulse according to the defibrillation impedance of the load 80, e.g., as described in U.S. Pat. No. 5,999,852, referenced earlier.

As an alternative to comparing two or more small signal impedance measurements (or other load-dependent electrical parameters) measured at different signal frequencies, it is also within the scope of the present invention to compare impedance measurements obtained using a small-amplitude signal and a high-amplitude signal (e.g., a defibrillation pulse). If the load is a patient, the small-amplitude and the high-amplitude impedance measurements will differ. If the load is a test device, the impedance measurements will be approximately equal. It may also be advantageous to apply a transformation equation to the small-amplitude measurement to obtain a "predicted" high-amplitude impedance. Comparing the predicted high-amplitude impedance with the actual measured high-amplitude impedance may yield information on the accuracy of the transformation equation, as well as information on the attachment of the electrodes to the load (i.e., on the quality of connection).

One implementation of the foregoing alternative embodiment may proceed as illustrated in FIG. 3, except that a high-amplitude signal is sent to the patient at block 38 instead of a small-amplitude signal. The small-amplitude and high-amplitude signal measurements are compared to each other at block 42, as shown, with the consequent actions shown at blocks 44 or 46 taking place depending on the outcome of decision block 42. A high-amplitude signal measurement may also be included in the impedance measurements obtained and evaluated in FIG. 4 using a voting scheme. The defibrillation pulse generator 78 shown in FIG. 5 may be used to provide the high-amplitude signal.

Various embodiments of the invention have been illustrated and described above. However, it will be appreciated by those of ordinary skill in the art that insignificant changes may be made therein that do not depart from the spirit and scope of the invention. For example, rather than using a cable 22 to directly connect a test device 20 to the defibrillator 10, as shown in FIG. 2, the electrodes 14a and 14b shown in FIG. 1 may be attached to receiving pads (not shown) on a test device 20 via cables 16a and 16b. Alternatively, the test device 20 may be integrated into the defibrillator 10 and be configured to receive and evaluate a defibrillation pulse discharged within the defibrillator if the terminal 18 of the defibrillator 10 is left unconnected.

It is also within the scope of the present invention to directly compare load-dependent electrical parameters derived from the small-amplitude signals applied to the load 80 (i.e., parameters other than load impedance measured in "ohms") to determine whether the load 80 is a patient 12 or a test device 20. For instance, a device operating according to the present invention may directly compare the voltage drop of the small signals applied to the load and determine that the load is a patient if the respective voltage drop measurements are different. Similarly, the device may directly compare current flow, energy delivered, calculated load-device time constant, or other load-dependent electrical parameters derived from the signals delivered to the load to determine if the load is a patient or a test device.

It will be further appreciated that the small signal impedance measurements determined by the impedance measuring unit 72 may be used for additional purposes, such as detection of motion in the load (i.e., when the load is a patient). The present invention may also be implemented in other types of medical devices designed to monitor and/or provide therapy to patients. The scope of the invention, therefore, should be determined in reference to the following claims, and equivalents thereto.

The embodiments of the invention in which an exclusive property or privilege is claimed are defined as follows:

1. A method for automatically determining whether a load connected to a defibrillator is a patient or a test device, comprising:

(a) delivering two or more small-amplitude signals at different frequencies to the load;

(b) obtaining small signal impedance measurements of the load based on the two or more small-amplitude signals delivered to the load;

(c) comparing the small signal impedance measurements to one another; and (d) determining that the load is a test device if the small signal impedance measurements are approximately equal, or that the load is a patient if the small signal impedance measurements are different.

2. The method of claim 1, further comprising predicting a defibrillation impedance of the load if the load is determined to be a patient, by applying a transformation equation to a small signal impedance measurement of the load.

3. The method of claim 2, further comprising delivering to the load a defibrillation pulse having a waveform characteristic based on the predicted defibrillation impedance of the load, if the load is determined to be a patient.

4. The method of claim 1, further comprising delivering to the load a defibrillation pulse having a waveform characteristic based on a small signal impedance measurement, if the load is determined to be a test device.

5. The method of claim 1, further comprising determining whether to store data in a memory when the load is determined to be a test device, which data is normally collected and stored in the memory when the load is determined to be a patient.

6. The method of claim 1, further comprising providing a voting scheme when three or more small signal impedance measurements of the load are obtained, wherein the voting scheme is used in comparing the three or more small signal impedance measurements to one another and determining whether the load is a test device or a patient.

7. A device that automatically determines whether a load connected to the device is a patient or a test device, comprising:

(a) a signal generator configured to deliver two or more small-amplitude signals at different frequencies to the load;

(b) an impedance measuring unit configured to obtain small signal impedance measurements of the load based on the two or more small-amplitude signals delivered by the signal generator; and (c) a processing unit in communication with the impedance measuring unit, wherein the processing unit is configured to receive and compare the small signal impedance measurements to one another to determine that the load is a patient if the small signal impedance measurements are different, or determine that the load is a test device if the small signal impedance measurements are approximately equal.

8. The device of claim 7, wherein the impedance measuring unit is integrated with the processing unit to jointly obtain the small signal impedance measurements of the load and compare the small signal impedance measurements to one another.

9. The device of claim 7, wherein the processing unit is further configured to predict a defibrillation impedance of the load if the load is determined to be a patient, the processing unit applying a transformation equation to a small signal impedance measurement of the load to predict the defibrillation impedance.

10. The device of claim 9, further including a defibrillation pulse generator configured to deliver to the load a defibrillation pulse having a waveform characteristic based on the predicted defibrillation impedance of the load, if the load is determined to be a patient.

11. The device of claim 7, further including a defibrillation pulse generator for delivering to the load a defibrillation pulse having a waveform characteristic based on a small signal impedance measurement of the load, if the load is determined to be a test device.

12. The device of claim 7, further including a memory in communication with the processing unit, wherein the processing unit is further configured to determine whether to store data in the memory when the load is determined to be a test device, which data is normally collected and stored in the memory when the load is determined to be a patient.

13. The device of claim 7, wherein the processing unit is further configured to implement a voting scheme if the signal generator delivers three or more small-amplitude signals to the load and the impedance measuring unit obtains three or more small signal impedance measurements of the load, the processing unit using the voting scheme to compare the small signal impedance measurements to one another and determine whether the load is a patient or a test device.

14. A method for automatically determining whether a load connected to a device is a patient or a test device, comprising:

(a) delivering to the load a plurality of small-amplitude signals, each having different frequencies;

(b) measuring a load-dependent electrical parameter of the load for each of the plurality of small-amplitude signals delivered to the load; and (c) comparing each of the load-dependent electrical parameters to one another, and if the load-dependent electrical parameters are approximately equal, then determining that the load is a test device, or if the load-dependent electrical parameters are different from one another, then determining that the load is a patient.

15. The method of claim 14, further comprising predicting a high-amplitude impedance measurement of the load, if the load is determined to be a patient, by:

(a) determining a small-amplitude impedance measurement of the load based on one or more of the load-dependent electrical parameters; and (b) applying a transformation equation to the small-amplitude impedance measurement of the load.

16. The method of claim 15, further comprising determining a waveform characteristic of a defibrillation pulse to be delivered to the patient based on the predicted high-amplitude impedance measurement.

17. The method of claim 14, further comprising using a voting scheme in comparing the measured load-dependent electrical parameters to one another and determining whether the load is a test device or a patient.

18. A device that automatically determines whether a load connected to the device is a patient or a test device, comprising:

(a) a signal generator configured to deliver to the load a plurality of small-amplitude signals, each having different frequencies; and (b) a processor configured to measure a load-dependent electrical parameter for each of the plurality of small-amplitude signals delivered to the load, the processor further configured to compare the measured load-dependent electrical parameters to one another and determine whether the load is a patient or a test device based on a relative difference between the measured load-dependent electrical parameters.

19. The device of claim 18, wherein the processor is further configured to implement a voting scheme if the signal generator delivers three or more small-amplitude signals to the load and the processor obtains three or more load-dependent electrical parameters of the load, the processor using the voting scheme to compare the load-dependent electrical parameters to one another and determine whether the load is a patient or a test device.

20. The device of claim 18, further including a memory, wherein the processor is further configured to determine whether to store data in the memory when the load is determined to be a test device, which data is normally collected and stored in the memory when the load is determined to be a patient.

21. A device that automatically determines whether a load connected to the device is a patient or a test device, comprising:

(a) a signal generator configured to deliver to the load at least one small-amplitude signal and at least one high-amplitude signal; and (b) a processor configured to measure a load-dependent electrical parameter for each of the low-amplitude and high-amplitude signals delivered to the load, the processor further configured to compare the measured load-dependent electrical parameters to one another and determine whether the load is a patient or a test device based on a relative difference between the measured load-dependent electrical parameters.

22. The device of claim 21, wherein the measured load-dependent electrical parameter is impedance of the load, the small-amplitude signal yielding a small-amplitude impedance measurement and the high-amplitude signal yielding a high-amplitude impedance measurement.

23. The device of claim 22, wherein the processor is further configured to predict a high-amplitude impedance of the load by applying a transformation equation to the small-amplitude impedance measurement, and compare the predicted high-amplitude impedance with the measured high-amplitude impedance.

* * * * *